(12) United States Patent
Yoshino et al.

(10) Patent No.: US 12,426,820 B2
(45) Date of Patent: Sep. 30, 2025

(54) BIOLOGICAL ELECTRODE

(71) Applicant: TATSUTA ELECTRIC WIRE & CABLE CO., LTD., Higashiosaka (JP)

(72) Inventors: Shinji Yoshino, Higashiosaka (JP); Koujirou Ikoma, Higashiosaka (JP)

(73) Assignee: TATSUTA ELECTRIC WIRE & CABLE CO., LTD., Higashiosaka (JP)

( * ) Notice: Subject to any disclaimer, the term of this patent is extended or adjusted under 35 U.S.C. 154(b) by 359 days.

(21) Appl. No.: 18/036,960

(22) PCT Filed: Nov. 17, 2021

(86) PCT No.: PCT/JP2021/042146
§ 371 (c)(1),
(2) Date: May 15, 2023

(87) PCT Pub. No.: WO2022/107784
PCT Pub. Date: May 27, 2022

(65) Prior Publication Data
US 2023/0414146 A1   Dec. 28, 2023

(30) Foreign Application Priority Data
Nov. 17, 2020 (JP) .................... 2020-190735

(51) Int. Cl.
*A61B 5/265* (2021.01)
*A61B 5/268* (2021.01)

(52) U.S. Cl.
CPC .............. *A61B 5/265* (2021.01); *A61B 5/268* (2021.01)

(58) Field of Classification Search
CPC ......... A61B 5/267; A61B 5/268; A61B 5/266; A61B 5/282; A61B 5/296
See application file for complete search history.

(56) References Cited

U.S. PATENT DOCUMENTS

| | | |
|---|---|---|
| 2004/0069654 A1 | 4/2004 | McLaughlin et al. |
| 2005/0131336 A1 | 6/2005 | Mori et al. |
| 2019/0320923 A1 | 10/2019 | Shinohara et al. |
| 2019/0387993 A1 | 12/2019 | Suzuki et al. |

FOREIGN PATENT DOCUMENTS

| | | | |
|---|---|---|---|
| EP | 3482683 A1 * | 5/2019 | ............ A61B 5/25 |
| JP | H0595922 A * | 4/1993 | |
| JP | H595922 A | 4/1993 | |
| JP | H6189919 A | 7/1994 | |
| JP | 2004512527 A | 4/2004 | |
| JP | 4171422 B2 | 10/2008 | |
| JP | 201988764 A | 6/2019 | |
| WO | 2018003697 A1 | 1/2018 | |
| WO | 2018163881 A1 | 9/2018 | |

* cited by examiner

*Primary Examiner* — Eun Hwa Kim
(74) *Attorney, Agent, or Firm* — The Webb Law Firm (57) ABSTRACT

Provided is a biological electrode including a polarizable electrode layer; and a non-polarizable electrode layer layered on the polarizable electrode layer. The non-polarizable electrode layer includes a first silver layer layered on the polarizable electrode layer; a polymer layer layered on the first silver layer; and a second silver layer layered on the polymer layer, and at least the second silver layer includes silver chloride.

3 Claims, 8 Drawing Sheets

Example 4
Average thichness of second silver layer : 81.3nm (65-92nm)
Average thichness of first silver layer : 180.7nm (163-205nm)

BIOLOGICAL ELECTRODE

CROSS-REFERENCE TO RELATED APPLICATIONS

This application is the United States national phase of International Patent Application No. PCT/JP2021/042146 filed Nov. 17, 2021, and claims priority to Japanese Patent Application No. 2020-190735 filed Nov. 17, 2020, the disclosures of which are hereby incorporated by reference in their entireties.

BACKGROUND OF THE INVENTION

Field of the Invention

The present invention relates a biological electrode.

Description of Related Art

Conventionally used has been a biological electrode in which silver and silver chloride are used. For example, Patent Literature 1 describes a biological electrode including: a polarizable electrode layer including, for example, carbon; and a non-polarizable electrode layer layered on the polarizable electrode layer and including silver and silver chloride. Such a biological electrode has such electrical properties that non-polarity of silver and silver chloride can reduce a contact impedance between the electrode and a body surface such as skin.

In addition, such a biological electrode is generally used as a disposable electrode designed to be disposed of after application to a single patient. Thus, it is preferable that the amount of silver used be reduced to reduce the production cost. For example, Patent Literature 2 proposes a method including: forming a silver deposited film on a surface of a polarizable electrode layer; and further converting silver on a surface of the silver deposited film into silver chloride by, for example, electroplating or chlorine plasma to form a non-polarizable electrode layer including silver and silver chloride. It is said that such a method can reduce the thickness of the non-polarizable electrode layer, that is, can reduce the amount of silver used.

CITATION LIST

Patent Literature

Patent Literature 1: JP 4171422 B
Patent Literature 2: JP 2004-512527 T

SUMMARY OF THE INVENTION

Technical Problem

The biological electrode as described above is generally stored in a state where a conductive gel layer, which is a layer to be brought into contact with a body surface such as skin, is attached to the non-polarizable electrode layer. This allows the biological electrode to be quickly applied to the skin or the like when used in a medical field or the like. However, during such storage, there is a risk that chloride ions included in the conductive gel layer and silver included in the non-polarizable electrode layer react with each other to produce silver chloride, thereby destabilizing the electrical properties of the biological electrode. This unstable tendency could become remarkable if the amount of silver included in the non-polarizable electrode layer is reduced.

A more preferable method for forming the non-polarizable electrode layer in terms of reducing the amount of silver used is a chlorination method including: forming a layer including metallic silver such as a silver-deposited film; and converting part of silver included in the layer into silver chloride using, for example, chlorine plasma, than a method in which a silver-silver chloride paste is applied. However, when the non-polarizable electrode layer to be formed has a small thickness, it becomes difficult to adjust the degree of conversion into silver chloride since, for example, chlorination unexpectedly proceeds excessively.

In view of the above circumstances, it is an object of the present invention to provide a biological electrode that is excellent in storage stability and relatively easily produced.

Solution to Problem

A biological electrode according to the present invention includes: a polarizable electrode layer; and a non-polarizable electrode layer layered on the polarizable electrode layer, in which the non-polarizable electrode layer includes: a first silver layer layered on the polarizable electrode layer; a polymer layer layered on the first silver layer; and a second silver layer layered on the polymer layer, and at least the second silver layer includes silver chloride.

According to such a configuration that the first silver layer is covered by the polymer layer and the second silver layer, the first silver layer is hardly affected by, for example, the conductive gel layer so that the biological electrode excellent in storage stability can be achieved. Further, even during chlorination at the time of production, this configuration allows the first silver layer to be hardly affected by the chlorination. On the other hand, the second silver layer formed outside the first silver layer is sufficiently subjected to chlorination by a chemical liquid generally used for chlorination. Thus, according to the above configuration, the biological electrode relatively easily produced can be achieved.

The biological electrode according to the present invention is preferably configured such that the second silver layer has a thickness that is 0.3 times or more and 3.0 times or less as large as a thickness of the polymer layer.

According to such a configuration that the thickness of the second silver layer is 0.3 times or more and 3.0 times or less as large as the thickness of polymer layer, the biological electrode more easily produced and more excellent in storage stability can be achieved.

The biological electrode according to the present invention is preferably configured such that the polymer layer has a thickness of 20 nm or more and 150 nm or less.

According to such a configuration that the thickness of the polymer layer is 20 nm or more and 150 nm or less, the biological electrode further excellent in storage stability can be achieved.

DESCRIPTION OF THE INVENTION

A description will be hereinafter given on a biological electrode according to one embodiment of the present invention with reference to the drawings.

A biological electrode 1 of this embodiment is used for acquiring biological information. Examples of such biological information include electrocardiogram, electroencephalography, and electromyography. The biological electrode 1, which is generally a disposable electrode to be disposed of after application to a single patient, can preferably be produced at low cost. To achieve this, it is preferable that the biological electrode 1 have a small amount of silver used and be capable of being easily produced. Hereinafter, non-ionized silver such as silver chloride can be referred to as metallic silver, and the metallic silver and silver as silver ion forming silver chloride can be collectively referred to as silver element.

Figure 1:
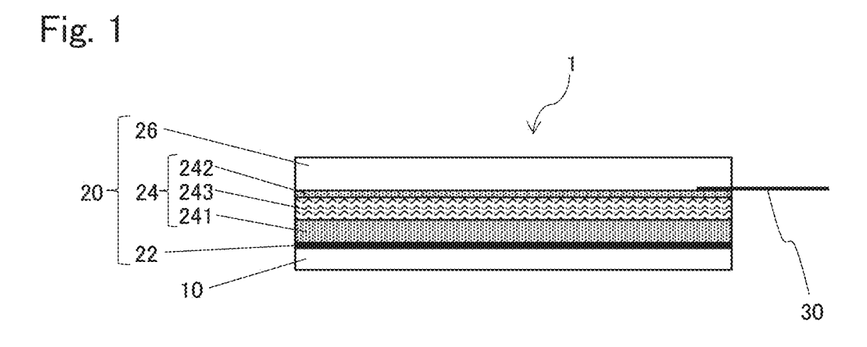
FIG. 1 is a schematic view of a sectional structure of a biological electrode according to one embodiment.
Figure 2:
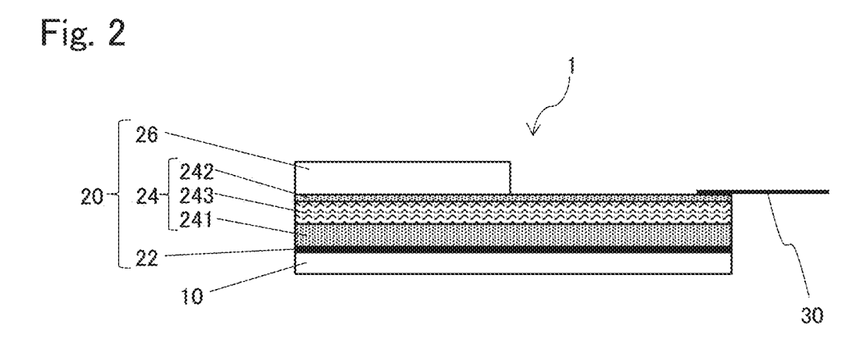
FIG. 2 is a schematic view of a sectional structure of a biological electrode having a lead wire connected to a position different from the lead wire in FIG. 1.
Figure 3:
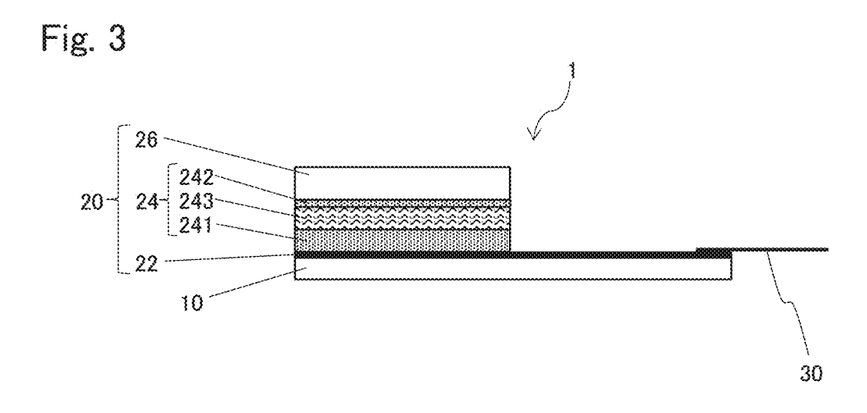
FIG. 3 shows a sectional structure of a biological electrode having a lead wire connected to a position different from the lead wire in FIG. 1 and FIG. 2.

As shown in FIG. 1 to FIG. 3, the biological electrode 1 includes an electrically insulated substrate layer 10 having a sheet shape, an electrode layer 20 layered on one surface of the substrate layer 10 and configured to detect electrical signals from a living body, and a lead wire 30 electrically connected to the electrode layer 20 and configured to transmit the electrical signals detected by the electrode layer 20 to a measuring instrument.

The substrate layer 10 is generally formed of an electrically insulating film made of polyethylene terephthalate (PET). The electrically insulating film herein refers to a film having a volume resistivity of $1 \times 10^{13}$ Ω·cm or more. The substrate layer 10 generally has a thickness of 5 to 100 μm.

The electrode layer 20 includes a polarizable electrode layer 22 layered on the one surface of the substrate layer 10, a non-polarizable electrode layer 24 layered on the polarizable electrode layer 22, and a conductive gel layer 26 attached to the non-polarizable electrode layer 24.

The polarizable electrode layer 22 includes graphite and/or carbon powder in addition to a resin. The thickness of the polarizable electrode layer 22 is generally 2 to 100 μm, preferably 3 to 50 μm, more preferably 4 to 20 μm.

The non-polarizable electrode layer 24 includes a first silver layer 241 directly layered on the polarizable electrode layer 22, a polymer layer 243 directly layered on the first silver layer 241, and a second silver layer 242 directly layered on the polymer layer 243.

The biological electrode 1 of this embodiment is stored in a state where the conductive gel layer 26 is attached to the second silver layer 242. Thus, the second silver layer 242 in particular might have the content of silver chloride increased by chloride ions in the conductive gel layer 26. This may change the electrical properties of the biological electrode 1 during storage. In this embodiment, in contrast, the first silver layer 241 is covered with the polymer layer 243 and the second silver layer 242. This configuration allows the first silver layer 241 to be hardly affected by the conductive gel layer 26. Thus, in the first silver layer 241, the content of the metallic silver set at the time of production can be easily maintained even during storage. As described above, the biological electrode 1 of this embodiment has stable electrical properties since at least the content of the metallic silver included in the first silver layer 241 is suppressed from being reduced during storage.

Out of the first silver layer 241 and the second silver layer 242, at least the second silver layer 242 includes silver chloride. The first silver layer 241 can include silver chloride.

It is preferable that the mass ratio of the metallic silver included in the first silver layer 241 (i.e., the mass ratio thereof to the total mass of the first silver layer 241) be larger than the mass ratio of the metallic silver included in the second silver layer 242 (i.e., the mass ratio thereof to the total mass of the second silver layer 242). In other words, it is preferable that the first silver layer 241 be richer in the metallic silver than the second silver layer 242. This configuration can secure a sufficient amount of the metallic silver that is not to be converted into silver chloride during storage.

It is preferable that the mass ratio of the silver chloride included in the second silver layer 242 (i.e., the mass ratio thereof to the total mass of the second silver layer 242) be larger than the mass ratio of the silver chloride included in the first silver layer 241 (i.e., the mass ratio thereof to the total mass of the first silver layer 241). In other words, it is preferable that the second silver layer 242 be richer in the silver chloride than the first silver layer 241.

In the biological electrode formed to have the non-polarizable electrode layer 24 including no polymer layer 243, there is a likelihood of degraded electrical properties of the biological electrode through, for example, reduced non-polarizability of the non-polarizable electrode layer when the amount of silver element used is attempted to be simply reduced (specifically, when each of the silver layers is attempted to be made to have a small thickness to reduce the amount of silver element used). In the biological electrode 1 of this embodiment, in contrast, the non-polarizable electrode layer 24 has the polymer layer 243 interposed between the first silver layer 241 and the second silver layer 242 to thereby allow the thicknesses of the first silver layer 241 and the second silver layer 242 to be reduced to nano level. Specifically, in terms of reducing the amount of silver used, the thickness of the first silver layer 241 can be 300 nm or less, and is more preferably 200 nm or less. The thickness of the second silver layer 242 can be 200 nm or less, and is more preferably 100 nm or less. Further, the total thickness of the first silver layer 241 and the second silver layer 242 is preferably 500 nm or less. The thickness of the first silver layer 241 is preferably 50 nm or more, and the thickness of the second silver layer 242 is preferably 30 nm or more. The total thickness is preferably 80 nm or more.

In order to ensure storage stability of the biological electrode 1 for a longer period of time, the content of the metallic silver included in the non-polarizable electrode layer 24 is preferably equal to or higher than a specific amount. For example, the thickness of the first silver layer 241 rich in the metallic silver is preferably larger than the thickness of the second silver layer 242.

In contrast, the thickness of the second silver layer 242 rich in the silver chloride is preferably as small as possible, and is preferably smaller than at least the thickness of the first silver layer 241. This allows the biological electrode 1 to have more excellent electrical properties.

An effect further expected to be produced by the biological electrode 1 when the thicknesses of the first silver layer 241 and the second silver layer 242 are reduced to nano level is that the biological electrode 1 can be configured to allow X-rays to sufficiently pass therethrough. Specifically, in medical practice, there are some cases where X-ray images are taken concurrently with a measurement such as an electrocardiographic measurement. In such cases, the biological electrode 1 of this embodiment hardly interferes with the observation of internal organs using the X-ray images. The biological electrode 1 configured as above can be suitable for use in X-ray examinations for children and fetuses having small internal organs.

The thickness of each of the first silver layer 241 and the second silver layer 242 can be obtained as an average thickness by cross-sectional observations using a scanning electron microscope (SEM). Specifically, the biological electrode 1 from which the conductive gel layer 26 has been removed is subjected to embedding using, for example, an epoxy resin and cross-section processing by an ion milling apparatus, to prepare a measurement sample. Next, the sample is placed inside the SEM to have a longitudinal direction of the first silver layer 241, the polymer layer 243, and the second silver layer 242 being parallel with a width direction of an image to capture a reflected electron image having a width of about 4 μm (a height of about 3.2 μm). In the SEM image, the thicknesses of a plurality of randomly selected positions (e.g., 9 positions) of each of the first silver layer 241 and the second silver layer 242 are measured, and the obtained values are arithmetically averaged to obtain the respective thicknesses.

The polymer layer 243 preferably includes a polymer based corrosion inhibitor. This configuration not only suppresses deterioration originating from the conductive gel layer 26, but also suppresses air intrusion into the first silver layer 241 to suppress deterioration of the first silver layer 241.

The polymer layer 243 preferably has such a thickness as not to interfere with exchange of ions or electrons between the first silver layer 241 and the second silver layer 242 at the time of use of the biological electrode 1. In this regard, the thickness of the polymer layer 243 is preferably 20 to 150 nm, more preferably 30 to 100 nm. This configuration allows the biological electrode 1 to have more excellent electrical properties. The thickness of the polymer layer 243 is measured with a measurement sample prepared in the same manner as in the case where the thickness of each of the first silver layer 241 and the second silver layer 242 is measured. Using the SEM, a reflected electron image is captured with its contrast and luminance adjusted so that the first silver layer 241 and the second silver layer 242 each have an RGB 256 gradation of 110 to 185 and the epoxy resin with the biological electrode embedded therein has an RGB 256 gradation of 20 to 70. Next, the captured image is binarized using image analysis software to obtain an image, and the area of a portion between the first silver layer 241 and the second silver layer 242 in the obtained image is determined by automatic analysis. Then, the area is divided by its length to determine the thickness of the polymer layer as an average thickness.

The thickness of the second silver layer 242 is preferably 0.3 times or more, more preferably 0.6 times or more, particularly preferably 0.9 times or more, as large as the thickness of the polymer layer 243. This configuration causes silver in the first silver layer 241 to be hardly converted into silver chloride in the chlorination treatment at the time of production, thereby making it further easier to produce the biological electrode 1. The thickness of the second silver layer 242 is preferably 3.0 times or less, more preferably 2.5 times or less, as large as the thickness of the polymer layer 243. This configuration can reduce the amount of silver element used while stabilizing the electrical properties of the biological electrode 1.

The corrosion inhibitor included in the polymer layer 243 includes a resin and a thermosetting agent.

Examples of the corrosion inhibitor include VM-AL, VM-C, VM-TOP, and NCU-30 (B), which are manufactured by Dainichiseika Color & Chemicals Mfg. Co., Ltd.

In terms of being excellent in preventing corrosion of silver element, examples of the resin include one, or two or more selected from the group consisting of a polyester-based resin, a urethane-based resin, an acrylic resin, an epoxy-based resin, a melamine-based resin, a styrene-based resin, a polyamide-based resin, a siloxane-based resin, a vinyl chloride-based resin, a vinyl acetate-based resin, a cellulose-based resin, a phenol-based resin, and the like. In terms of weather resistance, it is preferable that the resin include a polyester-based resin, an acrylic resin, a urethane-based resin, an epoxy-based resin, a melamine-based resin, and a cellulose-based resin.

The mass ratio of the resin to the total mass of the polymer layer 243 is generally 80 to 99.9%, preferably 85 to 99%, more preferably 90 to 95%.

Examples of the thermosetting agent include a commonly available thermosetting agent, such as one, or two or more selected from the group consisting of an isocyanate-based thermosetting agent, an epoxy-based thermosetting agent, an imidazole-based thermosetting agent, and the like. In terms of weather resistance and reactivity, it is preferable that the thermosetting agent include the isocyanate-based thermosetting agent. Examples of the isocyanate-based thermosetting agent include a TDI (tolylene diisocyanate) based agent, an XDI (xylene diisocyanate) based agent, an MDI (methylene diisocyanate) based agent, and an HMDI (hexamethylene diisocyanate) based agent.

The mass ratio of the thermosetting agent to the total mass of the polymer layer 243 is generally 0.1 to 20%, preferably 1 to 15%, more preferably 5 to 10%.

The conductive gel layer 26 is a layer that brings the biological electrode 1 into contact with the surface of the skin. The conductive gel layer 26 generally includes, as an electrolyte, an alkali metal halide such as sodium chloride or potassium chloride. A conventionally known gel layer can be used for the conductive gel layer 26. The conductive gel layer 26 is directly attached to the second silver layer 242.

A conventionally known lead wire can be used for the lead wire 30, which can be a wire having a metal conductor covered with a covering material, or a wire having a conductor formed of carbon fibers and covered with a covering material. As shown in FIG. 1, the lead wire 30 can be connected to the second silver layer 242 to have its one end sandwiched between the second silver layer 242 and the conductive gel layer 26. As shown in FIG. 2, when the conductive gel layer 26 does not cover the entire non-polarizable electrode layer 24 and a part of the non-polarizable electrode layer 24 is exposed, the lead wire 30 can have its one end connected to the exposed surface of the non-polarizable electrode layer 24. Further, as shown in FIG. 3, when the non-polarizable electrode layer 24 does not cover the entire polarizable electrode layer 22 and a part of the polarizable electrode layer 22 is exposed, the lead wire 30 can have its one end connected to the exposed surface of the polarizable electrode layer 22.

Next, a method for producing the biological electrode 1 will be described.

A method for producing the biological electrode 1 of this embodiment includes: a polarizable electrode layer forming step of forming the polarizable electrode layer 22 on one surface of the substrate layer 10 as the electrically insulating film made of PET; and a layering step of forming the non-polarizable electrode layer 24 on one surface of the polarizable electrode 22 to form a layered product.

In the polarizable electrode layer forming step, the polarizable electrode layer 22 is formed by coating the one surface of the substrate layer 10 with a carbon paste that includes graphite and/or carbon powder and an organic solvent in addition to the resin, followed by removing the organic solvent by drying.

The layering step includes: a first silver layer layering step of layering an untreated first silver layer before chlorination on a surface of the polarizable electrode layer 22 by a thin-film forming method such as a plating method or silver deposition to obtain a first layered body; a polymer layer layering step of layering the polymer layer 243 on the untreated first silver layer to obtain a second layered body; a second silver layer layering step of layering an untreated second silver layer before chlorination on the polymer layer 243 by the thin-film forming method to obtain a third layered body; and a chlorination step of converting part of silver included at least in the untreated second silver layer into silver chloride to form the non-polarizable electrode layer 24 and obtain the layered product.

Examples of the thin-film forming method in the first silver layer layering step include the wet plating method and the dry plating method. Examples of the wet plating method include the electrolytic plating method and the electroless plating method. Examples of the dry plating method include the vacuum vapor deposition method and the sputtering method. In terms of suppressing the production cost of the biological electrode 1, the dry plating method is preferable, and the vacuum vapor deposition method is more preferable. The dry plating method and the vacuum vapor deposition method enable each of the untreated first silver layer and the untreated second silver layer to have a relatively uniform thickness, which can thereby stabilize electrical properties of the biological electrode 1.

When the vacuum vapor deposition method is employed, it is preferable that silver thin films be formed at a pressure of $1 \times 10^{-2}$ Pa or less and a crucible temperature of 900 to 1600° C.

In the polymer layer layering step, the corrosion inhibitor is applied to the surface of the untreated first silver layer, followed by being subjected to heating treatment to harden the thermosetting agent included in the corrosion inhibitor to thereby form the polymer layer 243.

In the second silver layer layering step, the untreated second silver layer is layered on the surface of the polymer layer 243 by the thin-film forming method in the same manner as the first silver layer layering step to obtain the third layered body.

In the chlorination step, the third layered body is immersed in a chlorination treatment agent capable of converting silver into silver chloride to covert part of silver included at least in the untreated second silver layer of the third layered body into silver chloride to form the non-polarizable electrode layer 24. In so doing, part of silver included in the untreated first silver layer can be converted into silver chloride, or does not have to be converted into silver chloride.

Examples of the chlorination treatment agent preferably include an aqueous sodium chlorite solution and an aqueous sodium hypochlorite solution.

In the chlorination step, the chlorination treatment agent directly acts on the untreated second silver layer forming the surface of the third layered body, and thus the metallic silver can be quickly converted into silver chloride. This enables sufficient chlorination even when the chlorination treatment agent to be used is set to have a relatively low concentration and the duration of chlorination is set to be relatively short. For example, the chlorination treatment agent can have such a concentration as to allow only silver included in the untreated second silver layer to be converted into silver chloride. The duration for immersing the third layered body in the chlorination treatment agent can be, for example, 10 to 120 seconds. On the other hand, the concentration of the chlorination treatment agent and the duration of immersion can be set so as to further accelerate chlorination treatment. Even under such conditions, the metallic silver included in the untreated first silver layer is hardly converted into silver chloride since the layered product has the polymer layer 243 formed to cover the untreated first silver layer. As described above, the polymer layer 243 interposed between the first silver thin film and the second silver thin film makes it easy to set the amount of metallic silver included in the non-polarizable electrode layer 24 to a specific amount or more.

The temperature at which the third layered body is immersed in the chlorination treatment agent is generally 20 to 50° C.

In the chlorination step, the layered product is generally washed with water such as distilled water or ion exchange water, and then allowed to dry.

As a method for converting part of silver into silver chloride, the electrolytic method or chlorine vapor deposition in which a saline solution or hydrochloric acid is used can be employed.

The biological electrode 1 configured as above can sufficiently meet the requirements of the U.S. standard (ANSI/AAMI EC12:2000/(R)2010) even if it is formed to have a child size. A biological electrode having a small area as in the biological electrode having a child size tends to easily deteriorate its electrical properties, and has a likelihood of failing to sufficiently meet the requirements of the U.S. standard. The biological electrode 1 of this embodiment, in contrast, can sufficiently meet the U.S. standard even if it has such an area. The size of a biological electrode having a child size is generally a size having a contact area between a non-polarizable electrode layer 24 and a conductive gel layer 26 of 400 mm 2 or less, more preferably a size having a contact area of 300 mm 2 or less. For example, in the biological electrode 1 of this embodiment, DC offset-voltage (DC offset voltage, hereinafter referred to also as DC offset) ensures to be 100 mV or less, or can be a more preferable value of 10 mV. The AC impedance of the biological electrode 1 ensures to be 2,000Ω or less, or can be a more preferable value of 1,000Ω or less, 500Ω or less, or 200Ω or less. As to defibrillation overload recovery, the absolute value of polarization potential (hereinafter referred to also as SDR-4 times) of the biological electrode 1 after 5 seconds can be smaller than 100 mV, more preferably smaller than 20 mV, and the rate of change of the residual polarization potential (hereinafter referred to also as SDR-Slope) of the biological electrode 1 after 30 seconds can be smaller than ±1 mV/sec. Further, the impedance after defibrillation overload (hereinafter referred to also as SDR-Impedance) of the biological electrode 1 can be 2,000Ω or less, more preferably 200Ω or less.

The biological electrode 1 of this embodiment can maintain the performance as described above at room temperature for 2 years or more. For example, in an acceleration test at a temperature of 40° C., the biological electrode 1 can maintain the above performance for 3 weeks or more, 5 weeks or more, 7 weeks or more, or 10 weeks or more. Storage at 40° C. for 30 weeks is equivalent to storage at room temperature for 2 years.

As described above, a biological electrode 1 according to this embodiment includes: a polarizable electrode layer 22; and a non-polarizable electrode layer 24 layered on the polarizable electrode layer 22, in which the non-polarizable electrode layer 24 includes: a first silver layer 241 layered on the polarizable electrode layer 22; a polymer layer 243 layered on the first silver layer 241; and a second silver layer 242 layered on the polymer layer 243, and at least the second silver layer 242 includes silver chloride.

According to such a configuration that the first silver layer 241 is covered by the polymer layer 243 and the second silver layer 242, the first silver layer 241 is hardly affected by, for example, the conductive gel layer 26 so that the biological electrode 1 excellent in storage stability can be achieved. Further, even during chlorination at the time of production, this configuration allows the first silver layer 241 to be hardly affected by the chlorination. On the other hand, the second silver layer 242 formed outside the first silver layer 241 is sufficiently subjected to chlorination by a chemical liquid generally used for chlorination. Thus, according to the above configuration, the biological electrode 1 relatively easily produced can be achieved.

The biological electrode 1 according to this embodiment is preferably configured such that the second silver layer 242 has a thickness that is 0.3 times or more and 3.0 times or less as large as a thickness of the polymer layer 243.

According to such a configuration that the thickness of the second silver layer 242 is 0.3 times or more and 3.0 times or less as large as the thickness of polymer layer 243, the biological electrode 1 more easily produced and more excellent in storage stability can be achieved.

The biological electrode 1 according to this embodiment is preferably configured such that the polymer layer 243 has a thickness of 20 nm or more and 150 nm or less.

According to such a configuration that the thickness of the polymer layer 243 is 20 nm or more and 150 nm or less, the biological electrode 1 further excellent in storage stability can be achieved.

One embodiment as above has been described as an exemplification, but the biological electrode according to the present invention is not limited to the configuration of the aforementioned embodiment. Further, the biological electrode according to the present invention is not limited by the aforementioned operational effects, either. Various modifications can be made to the biological electrode according to the present invention without departing from the gist of the present invention.

EXAMPLES

Hereinafter, the present invention will be further described by way of Examples.

Example 1

(Polarizable Electrode Layer Forming Step)

A conductive carbon paste (UCC-2 manufactured by Nippon Graphite Industries, Co., Ltd.) was applied to one surface of an electrically insulating film made of PET as a material forming a substrate layer. The applied carbon paste was allowed to dry at 120° C. to form a polarizable electrode layer (having a thickness of 5 μm) on the one surface of the film.

(Layering Step)

The amount of silver and the amount of corrosion inhibitor assumed to be necessary for forming each of the layers were determined based on the target thickness values of the respective layers shown in Table 1 below, to form the layers. Specifically, first, an untreated first silver layer was formed by the vacuum vapor deposition method on the entire surface of the polarizable electrode layer. Next, a corrosion inhibitor including a polyester-based resin and an isocyanate-based thermosetting agent was applied to the entire surface of the untreated first silver layer. Subsequently, the applied corrosion inhibitor was heated to dry to form a polymer layer. Next, an untreated second silver layer was formed by the vacuum vapor deposition method on the entire surface of the polymer layer to prepare a third layered body. Then, the third layered body was immersed in a 0.02% sodium hypochlorite aqueous solution (at a temperature of 30 to 35° C. for 1 minute) to form a non-polarizable electrode layer. Thus, a layered product was obtained. The layered product was washed with distilled water, followed by being dried in a constant-temperature bath (120° C.). The thickness of each of the layers of the obtained layered product is shown in Table 2 below.

Examples 2 to 5

Layered products were each prepared in the same manner as in Example 1, except that the thicknesses (target thickness values) of the first silver layer, the second silver layer, and the polymer layer were set to the respective values shown in Table 1.

Comparative Example 1

A polarizable electrode layer was formed on a substrate layer in the same manner as in Example 1. Next, an untreated first silver layer was formed by the vacuum vapor deposition method on the entire surface of the polarizable electrode layer to form a first layered body. The first layered body was subjected to chlorination in the same manner as for the third layered body in Example 1, to obtain a layered product including a non-polarizable electrode layer including a first silver layer.

Figure 5:
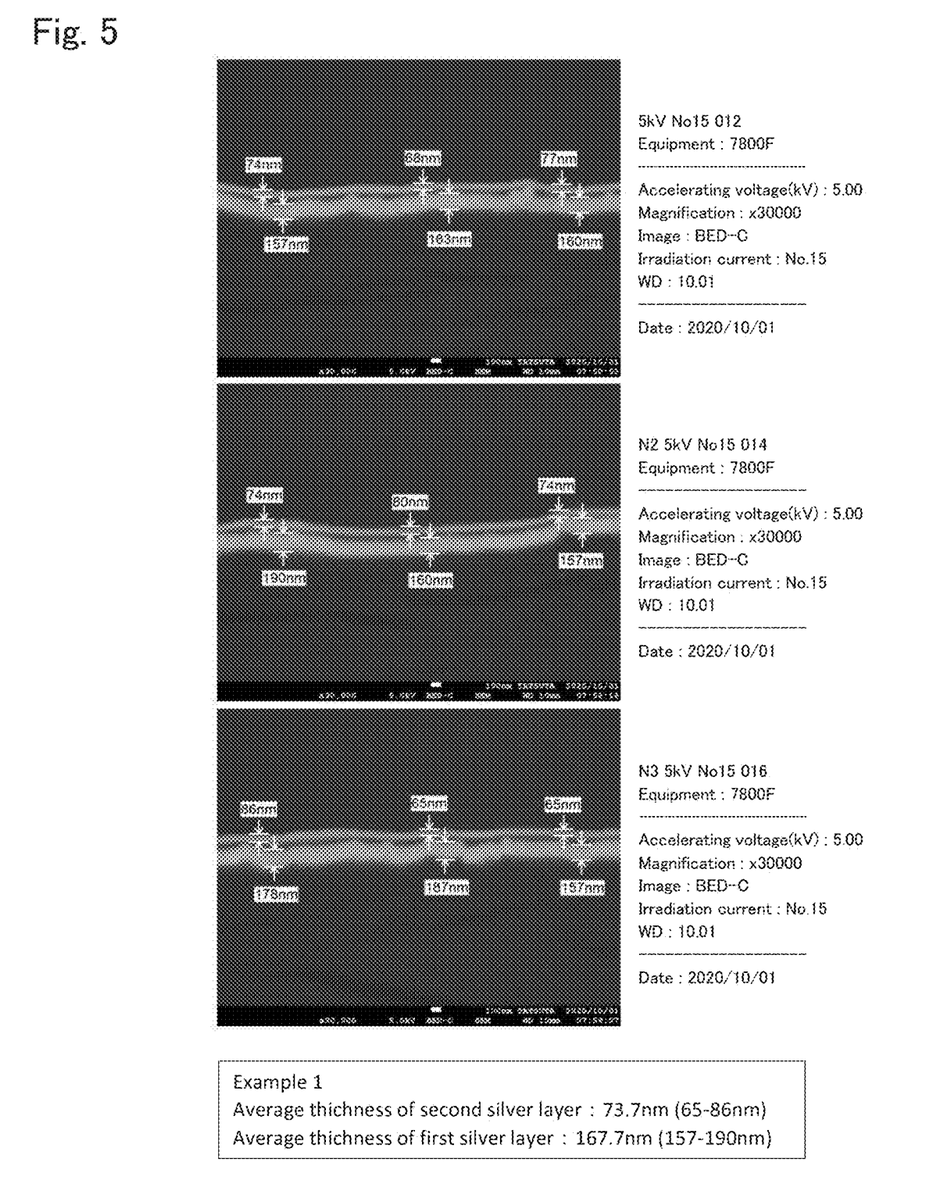
FIG. 5 shows measured values of the thickness of a first silver layer and the thickness of a second silver layer of Example 1, based on an SEM image.
Figure 6:
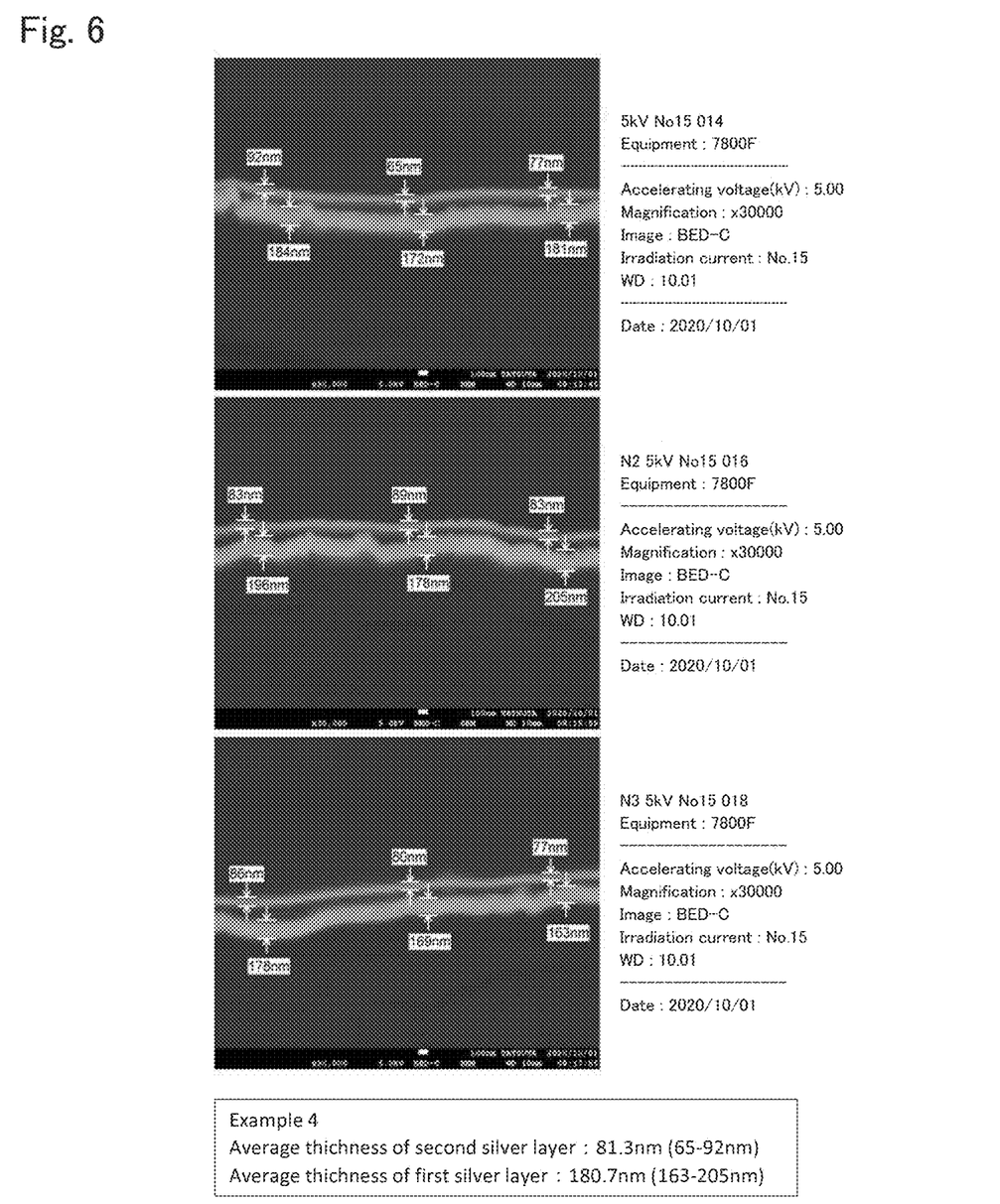
FIG. 6 shows measured values of the thickness of a first silver layer and the thickness of a second silver layer of Example 4, based on an SEM image.
Figure 7:
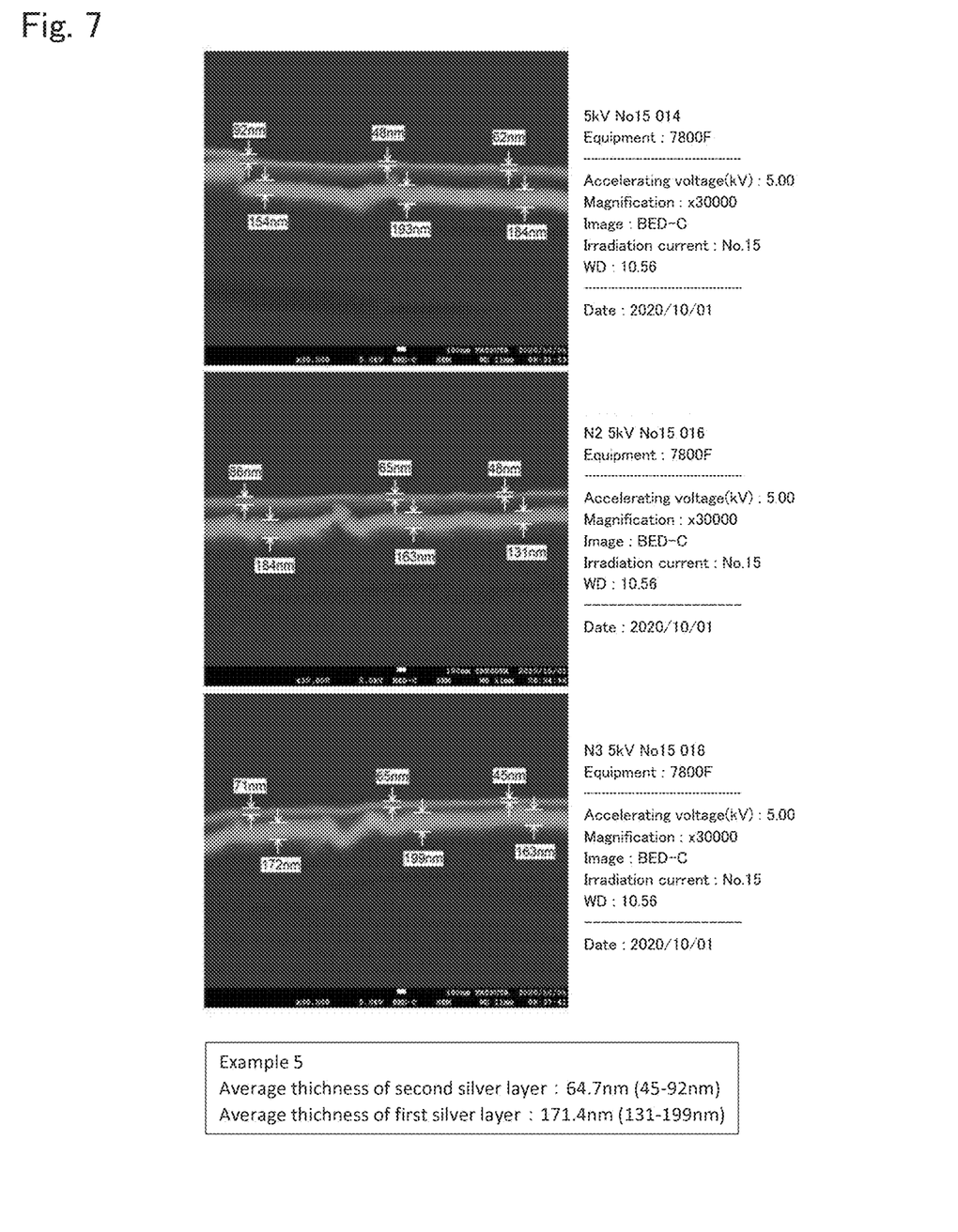
FIG. 7 shows measured values of the thickness of a first silver layer and the thickness of a second silver layer of Example 5, based on an SEM image.
Figure 8:
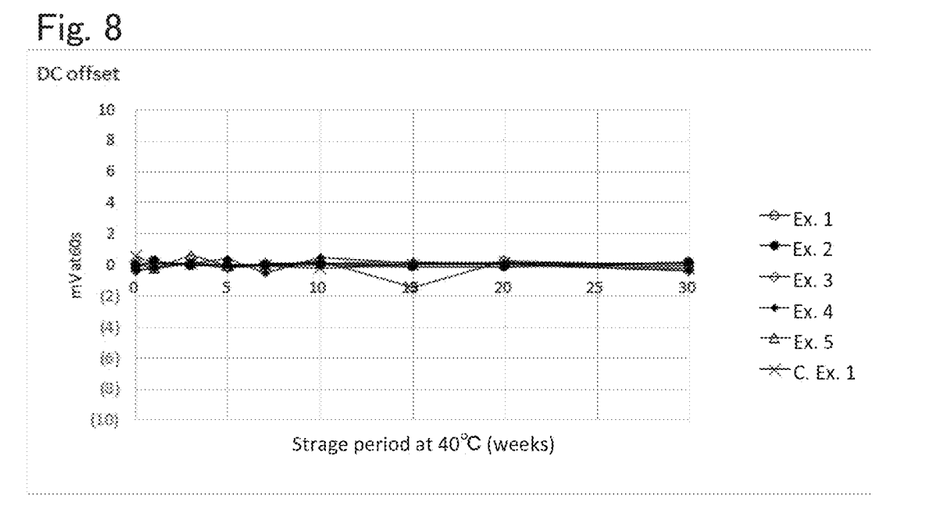
FIG. 8 is a graph showing the change with time in DC offset voltage of electrodes for evaluation in the Examples.
Figure 9:
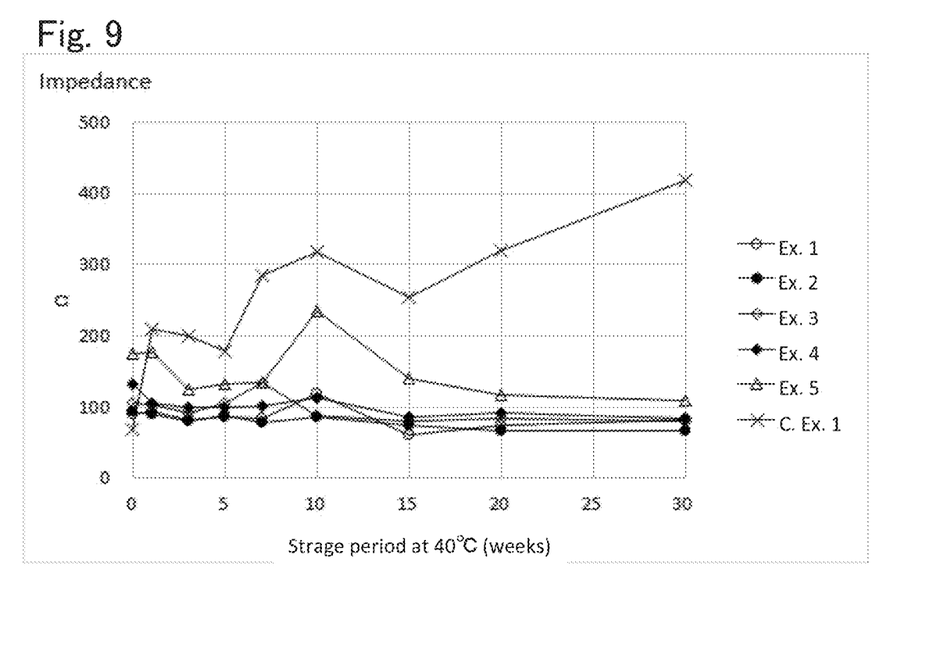
FIG. 9 is a graph showing the change with time in AC impedance of the electrodes for evaluation in the Examples.
Figure 10:
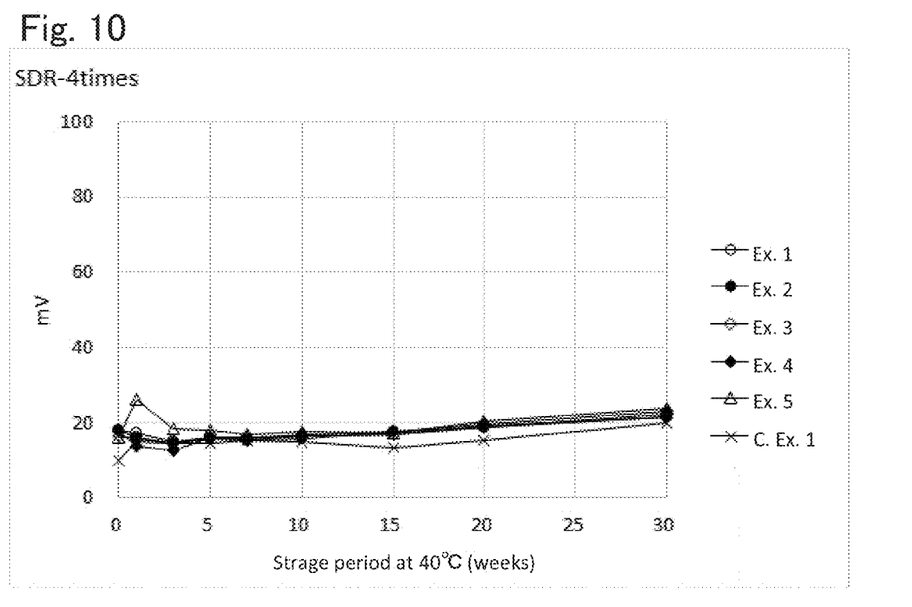
FIG. 10 is a graph showing the change with time in SDR-4times of the electrodes for evaluation in the Examples.
Figure 11:
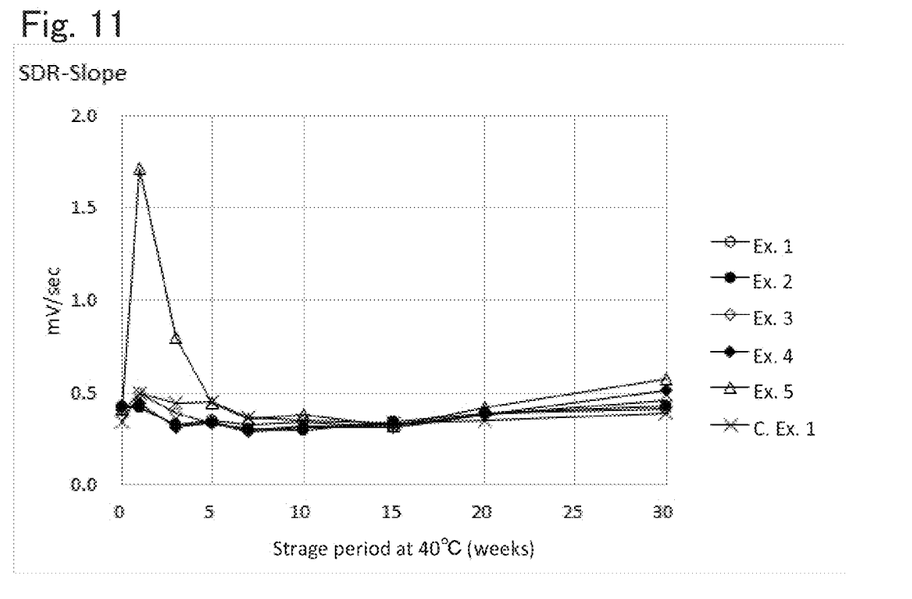
FIG. 11 is a graph showing the change with time in SDR-Slope of the electrodes for evaluation in the Examples.
Figure 12:
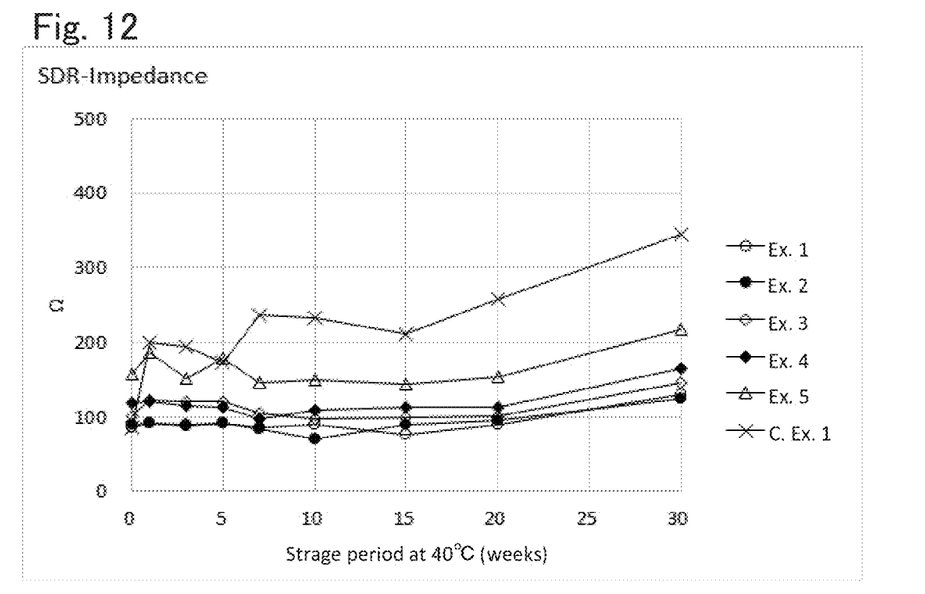
FIG. 12 is a graph showing the change with time in SDR-Impedance of the electrodes for evaluation in the Examples.

As for each of Examples 1, 4, and 5, cross-sectional observation was performed with an SEM, and the thickness of each of the layers was measured by the aforementioned method (SEM images in FIGS. 5 to 7). The results are shown in Table 2. A comparison between the measured values in Table 2 and the target values in Table 1 found a difference in the thickness of each of the polymer layers. This may be because a part of the corrosion inhibitor remained on a coating roller used for the application of the corrosion inhibitor.

TABLE 1

| | Target thickness values of layers (nm) | | |
|---|---|---|---|
| | First silver layer | Polymer layer | Second silver layer |
| Ex. 1 | 150 | 50 | 50 |
| Ex. 2 | 150 | 75 | 50 |
| Ex. 3 | 150 | 100 | 50 |
| Ex. 4 | 150 | 125 | 50 |
| Ex. 5 | 150 | 150 | 50 |
| C. Ex. 1 | 200 | — | — | of the cut pieces so as to allow their three corresponding end edges to overlap each other. Then, the conductive gel layers were further attached to each other to prepare a pair of electrodes for evaluation. The electrodes for evaluation were placed in an aluminum pack and stored in a constant-temperature bath set to 40° C. The observation of the electrodes for evaluation over time was performed for their electrical properties in accordance with the evaluation method of ANSI/AAMI EC12:2000. The results are shown in Table 3 and FIGS. 8 to 12.

TABLE 3

| | | Storage period at 40° C. (weeks) | | | | | | | | |
|---|---|---|---|---|---|---|---|---|---|---|
| | | 0 | 1 | 3 | 5 | 7 | 10 | 15 | 20 | 30 |
| Ex. 1 | DC offset | (0.0) | 0.1 | 0.0 | (0.1) | (0.0) | 0.2 | (1.4) | 0.3 | (0.1) |
| | Impedance | 89.8 | 93.9 | 82.5 | 86.9 | 84.5 | 118.8 | 61.4 | 73.4 | 82.6 |
| | SDR-4times | 18.0 | 17.4 | 14.8 | 16.2 | 16.2 | 16.6 | 16.9 | 19.0 | 21.3 |
| | SDR-Slope | 0.4 | 0.4 | 0.3 | 0.4 | 0.3 | 0.3 | 0.3 | 0.4 | 0.4 |
| | SDR-Impedance | 86.1 | 92.1 | 89.8 | 92.4 | 86.8 | 88.9 | 75.9 | 90.0 | 129.9 |
| Ex. 2 | DC offset | (0.1) | 0.3 | (0.0) | (0.0) | (0.1) | (0.0) | (0.1) | (0.1) | 0.2 |
| | Impedance | 93.7 | 89.0 | 80.1 | 88.1 | 78.7 | 86.7 | 75.0 | 67.3 | 67.0 |
| | SDR-4times | 17.9 | 15.9 | 14.3 | 15.6 | 15.2 | 15.8 | 17.6 | 18.8 | 21.6 |
| | SDR-Slope | 0.4 | 0.4 | 0.3 | 0.3 | 0.3 | 0.3 | 0.3 | 0.4 | 0.4 |
| | SDR-Impedance | 89.2 | 91.7 | 87.5 | 92.3 | 84.9 | 71.0 | 90.8 | 94.9 | 125.1 |
| Ex. 3 | DC offset | (0.4) | (0.2) | 0.2 | (0.2) | 0.1 | 0.1 | (0.0) | (0.0) | (0.4) |
| | Impedance | 105.7 | 104.0 | 91.9 | 105.3 | 133.7 | 88.8 | 79.6 | 83.4 | 79.4 |
| | SDR-4times | 16.5 | 15.6 | 14.5 | 16.0 | 15.3 | 16.5 | 16.9 | 18.8 | 22.1 |
| | SDR-Slope | 0.4 | 0.5 | 0.4 | 0.3 | 0.3 | 0.3 | 0.3 | 0.4 | 0.5 |
| | SDR-Impedance | 101.9 | 123.4 | 121.0 | 120.4 | 104.4 | 97.6 | 99.1 | 100.6 | 145.9 |
| Ex. 4 | DC offset | (0.4) | (0.2) | 0.1 | 0.4 | (0.5) | 0.5 | 0.1 | 0.1 | (0.4) |
| | Impedance | 132.7 | 105.9 | 98.7 | 99.3 | 101.5 | 112.8 | 85.5 | 91.2 | 83.9 |
| | SDR-4times | 17.7 | 13.6 | 12.7 | 15.9 | 15.5 | 17.0 | 17.6 | 19.3 | 23.1 |
| | SDR-Slope | 0.4 | 0.4 | 0.3 | 0.3 | 0.3 | 0.3 | 0.3 | 0.4 | 0.5 |
| | SDR-Impedance | 118.7 | 121.1 | 115.4 | 113.8 | 97.5 | 109.2 | 113.3 | 113.2 | 166.0 |
| Ex. 5 | DC offset | 0.0 | (0.2) | 0.6 | (0.0) | 0.0 | 0.1 | 0.2 | 0.1 | 0.1 |
| | Impedance | 174.8 | 176.7 | 124.2 | 132.3 | 134.6 | 234.7 | 139.4 | 117.0 | 109.7 |
| | SDR-4times | 16.1 | 26.2 | 18.2 | 18.1 | 16.8 | 17.6 | 17.1 | 20.4 | 24.0 |
| | SDR-Slope | 0.4 | 1.7 | 0.8 | 0.4 | 0.4 | 0.4 | 0.3 | 0.4 | 0.6 |
| | SDR-Impedance | 158.4 | 186.4 | 151.1 | 179.3 | 146.2 | 148.9 | 144.9 | 153.3 | 217.4 |
| C. Ex. 1 | DC offset | 0.6 | 0.1 | 0.1 | (0.0) | (0.0) | (0.2) | (0.0) | 0.2 | (0.2) |
| | Impedance | 69.1 | 210.5 | 199.7 | 178.9 | 285.9 | 317.9 | 253.8 | 320.7 | 417.5 |
| | SDR-4times | 9.8 | 14.9 | 14.4 | 14.6 | 15.1 | 15.0 | 13.4 | 15.4 | 20.0 |
| | SDR-Slope | 0.3 | 0.5 | 0.4 | 0.5 | 0.4 | 0.3 | 0.3 | 0.3 | 0.4 |
| | SDR-Impedance | 86.5 | 200.1 | 193.3 | 172.3 | 237.1 | 232.9 | 211.1 | 257.8 | 344.4 |

As shown in Table 3 and FIGS. 8 to 12, the electrodes for evaluation in Examples 1 to 5 maintained excellent electrical properties for 30 weeks from the beginning of storage, indicating their excellent storage stability.

TABLE 2

| | Measured thickness values of layers (nm) | | | Ratio of measured thickness values Second silver layer:Polymer layer |
|---|---|---|---|---|
| | First silver layer | Polymer layer | Second silver layer | |
| Ex. 1 | 167.7 | 32.5 | 73.7 | 2.27:1 |
| Ex. 4 | 180.7 | 81.9 | 81.3 | 0.99:1 |
| Ex. 5 | 171.4 | 118.4 | 64.7 | 0.55:1 |

[Evaluation Method]

Figure 4:
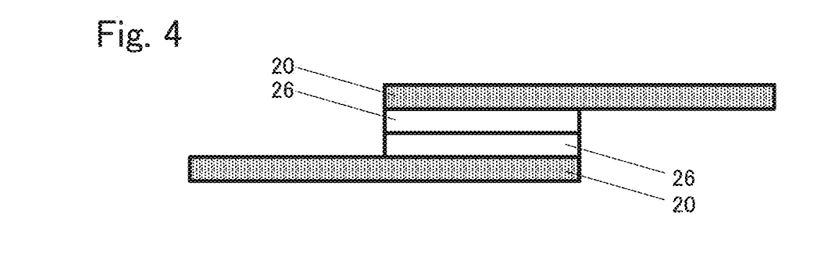
FIG. 4 is a view showing a state where examples are evaluated.

As shown in FIG. 4, each of the prepared layered products was cut into pieces of 15×30 mm (450 mm²), a conductive gel layer (CR-H manufactured by Sekisui Kasei Co., Ltd.) having a size of 15×15 mm (225 mm²) was attached to each

REFERENCE SIGNS LIST

1: Biological electrode
10: Substrate layer
20: Electrode layer
22: Polarizable electrode layer
24: Non-polarizable electrode layer
241: First silver layer
242: Second silver layer
243: Polymer layer
26: Conductive gel layer

30: Lead wire

The invention claimed is:

1. A biological electrode comprising:
a polarizable electrode layer; and
a non-polarizable electrode layer layered on the polarizable electrode layer, wherein
the non-polarizable electrode layer comprises: a first silver layer layered on the polarizable electrode layer; a polymer layer layered on the first silver layer; and a second silver layer layered on the polymer layer, and
at least the second silver layer comprises silver chloride.

2. The biological electrode according to claim 1, wherein the second silver layer has a thickness that is 0.3 times or more and 3.0 times or less as large as a thickness of the polymer layer.

3. The biological electrode according to claim 2, wherein the polymer layer has a thickness of 20 nm or more and 150 nm or less.

* * * * *